(12) United States Patent
Coca et al.

(10) Patent No.: US 7,638,542 B2
(45) Date of Patent: Dec. 29, 2009

(54) METHOD OF OBTAINING 2-AMINO-6-ALKYL-AMINO-4,5,6,7-TETRAHYDRO-BENZOTHIAZOLES

(75) Inventors: Gustavo Pascual Coca, Valladolid (ES); Jorge Martín Juárez, Valladolid (ES)

(73) Assignee: Ragactives, S.L., Valladolid (ES)

( * ) Notice: Subject to any disclaimer, the term of this patent is extended or adjusted under 35 U.S.C. 154(b) by 146 days.

(21) Appl. No.: 11/571,270

(22) PCT Filed: Jun. 24, 2005

(86) PCT No.: PCT/ES2005/000362

§ 371 (c)(1), (2), (4) Date: Feb. 19, 2007

(87) PCT Pub. No.: WO2006/003220

PCT Pub. Date: Jan. 12, 2006

(65) Prior Publication Data

US 2007/0161798 A1   Jul. 12, 2007

(30) Foreign Application Priority Data

Jun. 25, 2004  (ES)  ................................ 200401559

(51) Int. Cl.
A61K 31/381  (2006.01)
(52) U.S. Cl. ..................................... 514/367
(58) Field of Classification Search ............... 514/367
See application file for complete search history.

(56) References Cited

U.S. PATENT DOCUMENTS

| | | | |
|---|---|---|---|
| 3,682,945 | A | 8/1972 | Engelhart |
| 5,708,187 | A | 1/1998 | Flaugh et al. |
| 6,849,290 | B2 | 2/2005 | Makinen et al. |
| 2005/0059717 | A1 | 3/2005 | van Eupen et al. |
| 2006/0106224 | A1 | 5/2006 | Gupta et al. |

FOREIGN PATENT DOCUMENTS

| EP | 0 186 087 A1 | 7/1986 |
|---|---|---|
| EP | 0 207 696 A1 | 1/1987 |
| EP | 0749962 A1 | 12/1996 |

OTHER PUBLICATIONS

Vippagunta, et al. Advanced Drug Delivery Reviews. 48 (2001) 3-26.*
Schneider, et al. Journal of Medicinal Chemistry, 1987, 30, pp. 494-498.*
Gewald, K., et al., "Sulfure-heterocyclics and precursors. XXX. A simple synthesis of 2-amino thiazoles", "J. Prakt. Chem.", 1964, pp. 298-300, vol. 23, No. 5-6.
Gewald, K., et al, "On the reaction of enamines with sulfur and cyanamide", "J. Prakt. Chem.", 1970, pp. 776-779, vol. 312, No. 5.
Merck & Co., Inc., "7705. Pramipexole", "The Merck Index", 2008, p. 7707, Publisher: Merck Publishing.
European Medicines Agency, "Scientific Discussion: Approval of Mirapexin", "Scientific Discussion", Apr. 1, 2001, pp. 1-10, Publisher: European Medicines Agency; available at http://www.emea.europa.eu/humandocs/ Humans/EPAR/mirapexin/mirapexinM2.htm.
Schneider, C. et al., "Dopamine Autoreceptor Agonists: Resolution and Pharmacological Activity of 2,6-Diaminotetrahydrobenzothiazole and a Aminothiazole Analogue of Amorphine", "J. Med. Chemistry", 1987, pp. 494-498, vol. 30.

* cited by examiner

Primary Examiner—Rebecca L Anderson
Assistant Examiner—Shawquia Young
(74) Attorney, Agent, or Firm—Steven J. Hultquist; Intellectual Property Technology Law

(57) ABSTRACT

A process for preparing 2-amino-6-alkyl-amino-4,5,6,7-tetrahydrobenzothiazoles of formula (I)

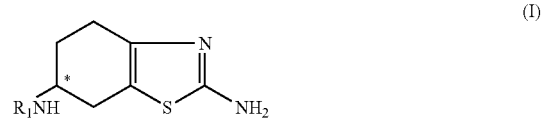

(I)

wherein the asterisk (*) represents an asymmetric carbon and $R^1$ is $C_1$-$C_6$ alkyl; and enantiomers and mixtures thereof, and their solvates, hydrates and pharmaceutically acceptable salts. The process involves (a) reacting

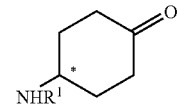

with a secondary amine, optionally in the presence of an acid and a first solvent, to form an enamine; (b) optionally removing the acid and first solvent, and then reacting the enamine with sulfur in the presence of a second solvent; and (c) reacting the previously obtained compound with cyanamide to obtain the formula (I) compound. Pramipexole, a dopamine D-2 agonist, can be made by such process, and is useful for the treatment of Parkinson's disease and schizophrenia.

16 Claims, No Drawings

METHOD OF OBTAINING 2-AMINO-6-ALKYL-AMINO-4,5,6,7-TETRAHYDRO-BENZOTHIAZOLES

CROSS-REFERENCE TO RELATED APPLICATIONS

This application is filed under the provisions of 35 U.S.C. §371 and claims the priority of International Patent Application No. PCT/ES2005/000362 filed 24 Jun. 2005, which in turn claims the priority of Spanish Patent Application No. P200401559 filed 25 Jun. 2004. The disclosures of said International Patent Application and said Spanish Patent Application are hereby incorporated herein by reference, in their respective entireties.

FIELD OF THE INVENTION

The invention relates to a process for preparing 2-amino-6-n-alkylamino-4,5,6,7-tetrahydrobenzothiazoles, their enantiomers or mixtures thereof, their solvates, hydrates or pharmaceutically acceptable salts; as well as to some of the intermediates of said process.

BACKGROUND OF THE INVENTION

Pramipexole, the generic name of the compound (S)-2-amino-6-n-propylamino-4,5,6,7-tetrahydrobenzothiazole, is a commercial product with dopamine D-2 agonist activity. The product is marketed in dihydrochloride form for treating Parkinson's disease and schizophrenia.

Pramipexole was described for the first time in patent EP 186 087. Said patent describes the obtainment of pramipexole and analogues the key reaction of which is halogen displacement of an alpha-halo-4-N-alkylamino-cyclohexanone (the halogen is generally bromine) by sulfur from thiourea and subsequent cycling on the ketone to give the aminothiazole ring. Patent EP 207 696 describes compounds related to pramipexole and the same synthetic approach is used. The drawback of both syntheses is that the preparation of the alpha-halo-4-N-alkylamino-cyclohexanone takes place with a poor yield.

Another synthetic approach to pramipexole is described in patent application WO 02 22950. In this case, the aminothiazole ring is synthesized similar to the synthesis in patent EP 186 087, by reacting thiourea with alpha-monobromo-1,4-cyclohexanedione derivatives and then introducing the n-propylamino group by reductive amination with sodium cyanoborohydride and n-propylamine. In both processes, bromine is used as a halogenation reagent with the subsequent risk involved as it is a very reactive and extremely toxic product. Furthermore, in patent application WO 02 22950 sodium cyanoborohydride is additionally used as a reduction reagent, which have problems due to decomposition in an acid medium, with the possibility of generating cyanhydric acid, an extremely poisonous reagent.

Therefore, there are problems in the known syntheses of pramipexole that are associated to the use of certain reagents the handling of which is hazardous, in addition to the low yields in some parts of the mentioned processes. Therefore a process is needed which in part or wholly eliminates said problems but which can also be applied at an industrial scale, providing a product with a good yield and quality.

SUMMARY OF THE INVENTION

The invention provides processes for preparing 2-amino-6-alkyl-amino-4,5,6,7-tetrahydrobenzothiazoles which overcome the drawbacks of the previously mentioned syntheses of the state of the art. It especially prevents using bromine. In an additional object, the invention relates to some of the intermediate compounds of the present process.

DETAILED DESCRIPTION OF THE INVENTION

In one embodiment, the invention provides a process for preparing 2-amino-6-alkyl-amino-4,5,6,7-tetrahydrobenzothiazoles of formula (I)

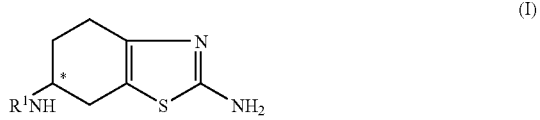

wherein the asterisk (*) indicates the presence of an asymmetric carbon and $R^1$ is a linear or branched $C_1$-$C_6$ alkyl group; their enantiomers or mixtures thereof, their solvates, hydrates or pharmaceutically acceptable salts, comprising the following steps:

(a) reacting a compound of formula (II)

wherein the asterisk (*) and $R^1$ have the previously mentioned meanings, with a secondary amine of formula $NHR^2R^3$ wherein $R^2$ and $R^3$ are, independently of one another, $C_1$-$C_3$ alkyl groups, or $R^2$ and $R^3$ together form a divalent $C_4$-$C_5$ radical, or a —$CH_2CH_2OCH_2CH_2$— radical, forming a cycle with the nitrogen atom to which it is attached;

optionally in the presence of an acid and a solvent 1, to form an enamine of formula (III)

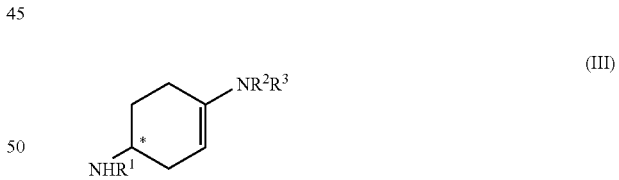

wherein the asterisk (*), $R^1$, $R^2$ and $R^3$ have the previously mentioned meanings;

(b) optionally removing said acid and said solvent 1, to then react the compound of formula (III) with sulfur in the presence of a solvent 2 to obtain the compound of formula (IV)

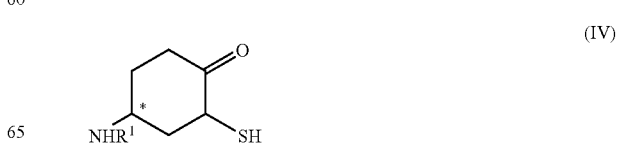

wherein the asterisk (*) and R$^1$ have the previously mentioned meanings, and finally (c) reacting the compound of formula (IV) with cyanamide to obtain the compound of formula (I).

The process of the invention for preparing 2-amino-6-alkyl-amino-4,5,6,7-tetrahydrobenzothiazoles of formula (I) can be carried out conventionally in three separate steps by the purification and/or isolation of the product obtained in each of them, or in a one pot sequence.

The first step (step a) of the process of the invention consists of forming an enamine of formula (III) by reacting the carbonyl group of the starting compound of formula (II) with a secondary amine, preferably cyclic such as pyrrolidine, morpholine, etc. Given that in the molecule there is an amine group having similar characteristics to the amines used for the synthesis of the target enamine, the authors of the present invention surprisingly have not detected polymerization compounds. The reaction is optionally carried out in the presence of an acid, for example p-toluenesulfonic acid, and a solvent 1, such as for example toluene, cyclohexane, diisopropylether, etc., preferably diisopropylether. The water formed as a reaction byproduct is preferably removed from the medium, for example by means of a Dean-Stark system, by adding dehydrating agents such as MgSO$_4$, etc. The reaction temperature is preferably between 10° C. and 90° C., more preferably between 40° C. and 50° C.

The second step (step b) of the process of the invention consists of introducing a mercaptan function in the cyclohexene ring. To that end, the acid and solvent 1 are preferably eliminated and the compound of formula (III) is reacted with sulfur in the presence of a solvent 2 to obtain the compound of formula (IV). Step b) is preferably carried out according to the following protocol: a solvent 2, for example an alcohol such as ethanol, methanol, propanol, isopropanol, etc., or dimethylformamide, is added to the residue obtained after eliminating the acid and solvent 1, the preferred solvent 2 being methanol. Then sulfur is added to the solution thus formed and the reaction is carried out at a temperature between −20° C. and 60° C., preferably between −5° C. and 10° C. with stirring for a time period between 5 minutes and 150 minutes, preferably between 10 minutes and 60 minutes.

The third step (step c) of the process of the invention consists of reacting the compound of formula (IV) obtained in the previous step with cyanamide to obtain the compound of formula (I). This reaction is preferably carried out by means of adding cyanamide to the mixture obtained in the previous step at a temperature comprised between −10° C. and 30° C., preferably between 0° C. and 5° C.

Each of these steps separately constitutes an embodiment of the invention. Therefore, in one aspect the invention is aimed at a process for preparing 2-amino-6-alkyl-amino-4,5,6,7-tetrahydrobenzothiazoles of formula (I)

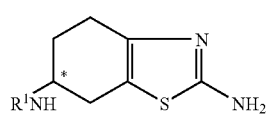

(I)

wherein the asterisk (*) indicates the presence of an asymmetric carbon and R$^1$ is a linear or branched C$_1$-C$_6$ alkyl group; its enantiomers or mixtures thereof, its solvates, hydrates or pharmaceutically acceptable salts, comprising reacting the compound of formula (IV):

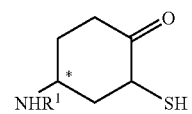

(IV)

wherein the asterisk (*) and R$^1$ have the previously mentioned meanings;

with cyanamide to obtain the compound of formula (I).

In another aspect, the invention is aimed at a process to form an enamine of formula (III)

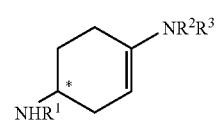

(III)

wherein the asterisk (*) indicates the presence of an asymmetric carbon; R$^1$ is a linear or branched C$_1$-C$_6$ alkyl group; and R$^2$ and R$^3$ are, independently of one another, C$_1$-C$_3$ alkyl groups, or R$^2$ and R$^3$ together form a divalent C$_4$-C$_5$ radical, or a —CH$_2$CH$_2$OCH$_2$CH$_2$— radical, forming a cycle with the nitrogen atom to which it is attached, comprising reacting a compound of formula (II)

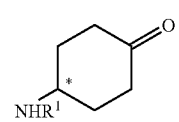

(II)

wherein the asterisk (*) and R$^1$ have the previously mentioned meanings;

with a secondary amine of formula NHR$^2$R$^3$, wherein R$^2$ and R$^3$ are those previously defined.

The synthesis process of the invention not only prevents using reagents the handling of which may be hazardous, but it also has yields exceeding 80%. Additionally, the final product is obtained with a high purity. In fact, the authors of the invention have found that the intermediate step of eliminating the acid and solvent 1 prevents the formation of impurities which give color to the end product of the process of the invention.

In another embodiment of the process of the invention, such process can be carried out in a one pot sequence, which implies a great advantage for its industrial-scale production. The process consists of dissolving the compound of formula (II) in a solvent and adding to the previous solution sulfur, cyanamide and a secondary amine of formula NHR$^2$R$^3$, wherein R$^2$ and R$^3$ are those previously defined, for example pyrrolidine, at a temperature between −10° C. and 50° C., preferably −5° C. and 20° C. In this case, the solvent is preferably an alcohol, for example methanol, ethanol or isopropanol.

In this embodiment, the secondary amine can be disregarded if desired given that the compound of formula (II) has a secondary amino group.

In a particular embodiment of the invention, after obtaining the compound of formula (I), the separation of the desired (R) or (S) enantiomer is carried out. Conventional optic resolution methods can be used to that end, for example by means of fractional crystallization of diastereoisomeric salts of both enantiomers using L-(+)-tartaric acid for example.

It is also possible to convert the compound of formula (I) obtained according to the process of the invention into a pharmaceutically acceptable salt thereof. Said salts are generally prepared, for example, by reacting the corresponding basic form of said compound with a stoichiometric amount of the suitable acid in water, in an organic solvent or in a mixture of both. Usually, the preferred non-aqueous solvents are ether, ethyl acetate, ethanol, isopropanol or acetonitrile. Included among the acid addition salts are mineral acid addition salts such as hydrochloride, hydrobromide, hydroiodide, sulfate, nitrate and phosphate, and organic acid addition salts such as acetate, maleate, fumarate, lactate, citrate, oxalate, succinate, tartrate, malate, mandelate, methanesulfonate and p-toluenesulfonate.

The compound of formula (I) can be obtained in free base or salt form. In both cases, it is preferably obtained in crystalline form, both as free compounds and as solvates (for example, hydrates), both forms being included in the scope of the present invention. The salvation methods are generally known in the state of the art.

The starting material for the proposed synthesis processes is a compound of formula (II). This compound can be reached starting from a monoprotected 1,4-cyclohexanedione of general formula (IIa):

wherein $R^5$ and $R^6$ form a carbonyl-protecting group.

Although any carbonyl-protecting group which is not affected by the reductive amination reaction can be used, preferably the $R^5$ and $R^6$ protecting groups are formed by alkyl or benzyl groups or $R^5$ and $R^6$ together form with the two oxygen atoms a $C_2$-$C_5$ alkanedioxy group. The alkyl groups preferably have from 1 to 6 carbon atoms, and they can be linear or branched. The preferred alkyl groups are methyl, ethyl, n-propyl, and t-butyl. Some of these products are commercial products.

The reaction of this compound of formula (IIa) with an alkylamine, such as an amine of formula $R^1NH_2$, wherein $R^1$ has the previously mentioned meaning, preferably n-propylamine, in the presence of a reducing agent constitutes reductive amination and gives rise to the compound of formula (IIb). Although any suitable reducing agent can be used in said reduction, the reaction is preferably carried out in the presence of hydrogen and a metallic catalyst, optionally supported such as Pd/C, or alternative by reacting the intermediate imine with a reducing agent such as $NaBCNH_3$ or $NaB(OAc)_3H$, more preferably $NaB(OAc)_3H$.

These reactions are carried out in an organic solvent, alcohols being preferable for the case that a metallic catalyst is used, more preferably the alcohols isopropanol, ethanol and methanol, and even more preferably ethanol; the preferred temperature being between 0° C. and 100° C., more preferably between 20° C. and 40° C.

In the event that the reduction is carried out with $NaB(OAc)_3H$, the solvents can be ethers, for example tetrahydrofuran (THF), halogenated hydrocarbides, for example dichloromethane, acetonitrile, or others. Nevertheless, the preferred solvent is tetrahydrofuran, in this case the preferred temperature being between −10° C. and 40° C., more preferably between 0° C. and 5° C.

In the event that the reduction is carried out with $NaBCNH_3$, the solvents can be alcohols such as methanol, ethanol, etc., acetonitrile, dimethylformamide, tetrahydrofuran or carboxylic acids, although the preferred solvent is methanol.

Reductive amination occurs in any of the cases with yields exceeding 95%.

The amine of formula (IIb)

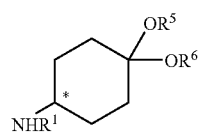

wherein the asterisk (*), $R^1$, $R^5$ and $R^6$ have the previously mentioned meanings, obtained by this process can be used in the next step without needing to be purified, or it can be purified by the formation of a salt, reacting it with an organic acid such as, for example, oxalic acid, or an inorganic acid such as, for example, hydrochloric acid, etc., in a suitable solvent, for example an alcohol such as isopropanol, or an ether such as tetrahydrofuran.

The compound of formula (II), the starting material of step a) of the process of the invention, is prepared by eliminating the carbonyl-protecting group in compound (IIb). Removal of the carbonyl-protecting group is preferably carried out in an acid medium in the presence of water, wherein the acid can be organic, such as p-toluenesulfonic acid or pyridinium p-toluenesulfonate, or it can be inorganic, for example hydrochloric acid or perchloric acid, etc., preferably hydrochloric acid. The reaction can be carried out in the presence of an organic solvent miscible with water, such as an alcohol, for example methanol, ethanol, propanol, etc., or tetrahydrofuran, acetonitrile, etc. The deprotection reaction is preferably carried out at a temperature comprised between 20° C. and 100° C., more preferably between 80° C. and 90° C.

In an additional object, the invention relates to some of the intermediate compounds of the present process. The invention specifically relates to the compounds of formula (III):

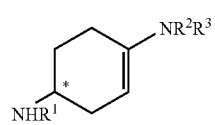

wherein the asterisk (*), $R^1$, $R^2$ and $R^3$ have the previously mentioned meanings. These compounds are generated as a product in step a) of the process of the invention. $R^2$ and $R^3$ preferably form a ring with the nitrogen. In a particular embodiment, $R^2$ and $R^3$ together form a —$CH_2CH_2CH_2CH_2$— radical.

The invention also relates to the compounds of formula (IV)

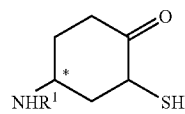

wherein the asterisk (*) and $R^1$ have the previously mentioned meanings. These compounds are generated as a product of step b) of the process of the invention.

The following examples illustrate different embodiments of the invention and should not be considered as limiting of the scope thereof.

EXAMPLE 1

Preparation of 4-n-propylaminocyclohexanone ethylene ketal oxalate

A solution of 1,4-cyclohexanedione monoethylene ketal (156 g, 1 mol) in THF (450 mL), n-propylamine (59 g, 82 mL, 1 mol) and AcOH (57 mL, 1 mol) is added dropwise to a suspension at −10° C. of NaB(OAc)$_3$H in 1.1 L of THF.

The reaction is left to slowly reach room temperature and reaction control is carried out. If the reaction has concluded, 100 mL of 10% NaOH are added and the mixture stirred. The phases are decanted and the aqueous phase is washed twice with CH$_2$Cl$_2$ (50 mL). The organic phase is washed twice with saturated NaCl aqueous solution (50 mL) and is dried with sodium sulfate.

A solution of oxalic acid (132 g, 1.5 mol) in MeOH (200 mL) is slowly added to the solution obtained and cooled at 0/5° C. The suspension is stirred for 30 minutes and is filtered on a plate.

$^1$H-NMR (DMSO): 0.74 (3H, t), 1.35-1.52 (m, 6H), 1.67-1.74 (m, 2H), 1.88-1.95 (m, 2H), 2.80 (dd, 2H), 3.81 (m, 4H) ppm.

$^{13}$C-NMR (DMSO): 10.26 (CH$_3$), 19.44, 25.97, 31.62, 46.66, 55.10 (CH), 64.10 (—O—CH$_2$—), 64.20 (—O—CH$_2$—), 107.76 (O—C—O), 165.53 (oxalic C=O) ppm.

EXAMPLE 2

Preparation of 4-n-propylaminocyclohexanone ethylene ketal oxalate

N-propylamine (88.5g, 123 mL, 1.5 mol) is added to a solution of 1,4-cyclohexanedione monoethylene ketal (156 g, 1 mol) in ethanol (780 mL). 5% Pd/C (50% water) is added to the mixture. The mixture is hydrogenated at 3 bar for several hours. Once the reaction has ended, the solvent is eliminated and the residue is dissolved in isopropanol (1.560 mL). A solution of oxalic acid (132 g, 1.5 mol) in MeOH (200 mL) is added dropwise to this solution. The suspension is stirred for 30 minutes and filtered on a plate, obtaining 274 g (95%).

EXAMPLE 3

N,N-4-oxocyclohexyl-n-propylamine

10% HCl (78 mL) is added to a solution of 4-n-propylaminocyclohexanone ethylene ketal oxalate (157 g, 0.85 mol) in water (470 mL). The solution is heated at 95° C.-100° C. in an inert atmosphere for 3 hours. Once the reaction ended, the pH is adjusted to 13-14 with 50% NaOH and the aqueous phase is extracted several times with CH$_2$Cl$_2$. The extracts are washed with saturated NaCl aqueous solution and the solvent is eliminated under vacuum. 84 g (99%) are obtained.

$^1$H-NMR (CDCl$_3$): 0.85 (t, 3H), 1.44 (sx, 2H), 1.53-1.64 (m, 2H), 1.98-2.70 (m, 2H), 2.18-2.28 (m, 2H), 2.36-2.44 (m, 2H), 2.50-2.56 (dd, 2H), 2.84-2.90 (m, 1H) ppm.

$^{13}$C-NMR (CDCl$_3$): 12.02 (CH$_3$), 23.64, 32.28 (2C), 38.81 (2C), 49.64, 54.09 (CH), 211.83 (C=O) ppm.

EXAMPLE 4

Pramipexole Base

Pyrrolidine (300 g, 355 mL, 4.25 mol) and p-toluenesulfonic acid.H$_2$O (3.23 g, 0.017 mol) is added to a solution of N,N-4-oxocyclohexyl-n-propylamine (133 g, 0.86 mol) in diisopropylether (1.3 L). The reaction mixture is stirred at 40° C. for 2 hours. Then anhydrous MgSO$_4$ (400 g) is added and stirred for an additional 10 hours.

After this time the suspension is filtered and the solid is washed with diisopropylether (200 mL). The solvent is eliminated under reduced pressure. Once the solvent is eliminated, MeOH (270 mL) is added. Sulfur (32.9 g, 1.2 mol) is added to the solution, stirring for 1 hour. After this time the mixture is cooled at 0/5° C. and a solution of cyanamide (36.5 g, 0.87 mol) in MeOH (180 mL) is added to the same. The reaction mixture is maintained at 0/5° C. for 3 hours and after this time it is left to reach room temperature (20° C.-22° C.), maintaining these conditions for an additional 10 hours.

The reaction mixture is cooled at 0° C.-5° C. and is stirred in these conditions for 2 hours. The resulting suspension is filtered, obtaining 139 g (77%) of base pramipexole with a purity of 98.5% (HPLC).

EXAMPLE 5

Pramipexole Base

Sulfur (20.5 g, 0.64 mol), cyanamide (26.9 g, 0.64 mol) and pyrrolidine (0.45 g, 0.53 mL, 6.4 mmol) are added to a solution of N,N-4-oxocyclohexyl-n-propylamine (100 g, 0.64 mol) in isopropanol (200 mL). The resulting suspension is stirred for several hours at a temperature between 10° C. and 20° C. Once the reaction ended, ethyl acetate (400 mL) is added to the suspension and the mixture is cooled for 2 hours between 0° C. and 5° C.

The resulting suspension is filtered, obtaining 100 g (73%) of pramipexole base with a purity of 98% (HPLC).

EXAMPLE 6

Pramipexole Base

Sulfur (2.05 g, 64 mmol) and cyanamide (2.69 g, 64 mmol) are added to a solution of N,N-4-oxocyclohexyl-n-propylamine (10 g, 64 mmol) in isopropanol (20 mL). The resulting suspension is stirred for several hours at a temperature between 10° C. and 20° C. Once the reaction ended, ethyl acetate (40 mL) is added to the suspension and the mixture is cooled for 2 hours between 0° C. and 5° C.

The resulting suspension is filtered, obtaining 9.5 g (70%) of pramipexole base with a purity of 97% (HPLC).

The invention claimed is:

1. A process for preparing 2-amino-6-alkyl-amino-4,5,6,7-tetrahydrobenzothiazoles of formula (I)

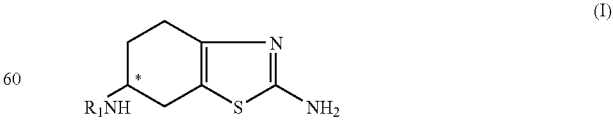

wherein the asterisk (*) indicates the presence of an asymmetric carbon and R$^1$ is a linear or branched C$_1$-C$_6$ alkyl group; their enantiomers or mixtures thereof, hydrates of pramipexole or pharmaceutically acceptable salts, comprising the following steps:

(a) reacting a compound of formula (II)

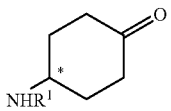

(II)

wherein the asterisk (*) and $R^1$ have the previously mentioned meanings, with a secondary amine of formula $NHR^2R^3$ wherein $R^2$ and $R^3$ are, independently of one another, $C_1$-$C_3$ alkyl groups, or $R^2$ and $R^3$ together form a divalent $C_4$-$C_5$ radical, or a —$CH_2CH_2OCH_2CH_2$— radical, forming a cycle with the nitrogen atom to which it is attached;
optionally in the presence of an acid and a solvent 1, to form an enamine of formula (III)

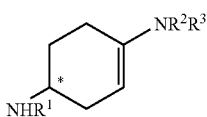

(III)

wherein the asterisk (*), $R^1$, $R^2$ and $R^3$ have the previously mentioned meanings;

(b) optionally removing said acid and said solvent 1, and then reacting the compound of formula (III) with sulfur in the presence of a solvent 2 to obtain the compound of formula (IV)

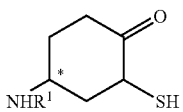

(IV)

wherein the asterisk (*) and $R^1$ have the previously mentioned meanings, and finally (c) reacting the compound of formula (IV) with cyanamide to obtain the compound of formula (I).

2. A process for preparing 2-amino-6-alkyl-amino-4,5,6,7-tetrahydrobenzothiazoles of formula (I)

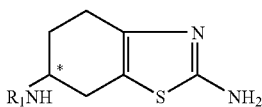

(I)

wherein the asterisk (*) indicates the presence of an asymmetric carbon and $R^1$ is a linear or branched $C_1$-$C_6$ alkyl group; their enantiomers or mixtures thereof, hydrates of pramipexole or pharmaceutically acceptable salts,
comprising reacting a compound of formula (II)

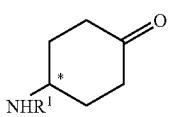

(II)

wherein the asterisk (*) and $R^1$ have the previously mentioned meanings, with sulfur and cyanamide in the presence of a solvent 2 and a secondary amine of formula $NHR^2R^3$ wherein $R^2$ and $R^3$ are, independently of one another, $C_1$-$C_3$ alkyl groups, or $R^2$ and $R^3$ together form a divalent $C_4$-$C_5$ radical, or a —$CH_2CH_2OCH_2CH_2$— radical, forming a cycle with the nitrogen atom to which it is attached.

3. A process according to claim 1, wherein the solvent 2 comprises an alcohol.

4. A process according to claim 2, wherein said secondary amine of formula $NHR^2R^3$ is substituted by said compound of formula (II).

5. A process according to claim 1, comprising the additional step of separating the mixture of enantiomers.

6. A process according to claim 1, comprising the additional step of converting the compound of formula (I) into a pharmaceutically acceptable salt thereof.

7. A process according to claim 1, wherein the compound of formula (II) is prepared by eliminating the carbonyl-protecting group from a compound of formula (IIb)

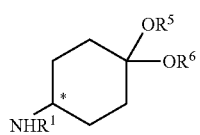

(IIb)

wherein the asterisk (*) indicates the presence of an asymmetric carbon, $R^1$ is a linear or branched $C_1$-$C_6$ alkyl group, and $R^5$ and $R^6$ form a carbonyl-protecting group.

8. A process according to claim 7, comprising preparing the compound of formula (IIb) by reductive amination of a compound of formula (IIa)

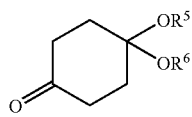

(IIa)

wherein $R^5$ and $R^6$ form a carbonyl-protecting group.

9. A process according to claim 1, wherein $R^1$ is n-propyl.

10. A process according to claim 9, wherein the compound of formula (I) is pramipexole or, hydrates of pramipexole or pharmaceutically acceptable salts.

11. A process for preparing 2-amino-6-alkyl-amino-4,5,6,7-tetrahydrobenzothiazoles of formula (I)

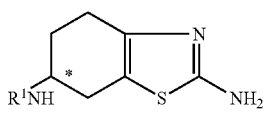

(I)

wherein the asterisk (*) indicates the presence of an asymmetric carbon and $R^1$ is a linear or branched $C_1$-$C_6$ alkyl group; their enantiomers or mixtures thereof, hydrates of pramipexole or pharmaceutically acceptable salts, comprising reacting a compound of formula (IV)

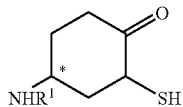 (IV)

wherein the asterisk (*) and R¹ have the previously mentioned meanings, with cyanamide to obtain the compound of formula (I).

12. A process according to claim 1, wherein the solvent 2 comprises methanol.

13. A process according to claim 2, comprising the additional step of separating the mixture of enantiomers.

14. A process according to claim 2, comprising the additional step of converting the compound of formula (I) into a pharmaceutically acceptable salt thereof.

15. A process according to claim 2, wherein the compound of formula (II) is prepared by eliminating the carbonyl-protecting group from a compound of formula (IIb).

16. A process according to claim 2, wherein R¹ is n-propyl.

* * * * *

UNITED STATES PATENT AND TRADEMARK OFFICE
CERTIFICATE OF CORRECTION

PATENT NO.       : 7,638,542 B2                                        Page 1 of 1
APPLICATION NO.  : 11/571270
DATED            : December 29, 2009
INVENTOR(S)      : Gustavo Pascal Coca It is certified that error appears in the above-identified patent and that said Letters Patent is hereby corrected as shown below:

Column 5, line 19: "salvation" should be -- solvation --.

Signed and Sealed this

Sixth Day of April, 2010

David J. Kappos
*Director of the United States Patent and Trademark Office*